United States Patent
Cabelka et al.

(10) Patent No.: US 8,050,763 B2
(45) Date of Patent: *Nov. 1, 2011

(54) ISOLATION CIRCUITRY AND METHOD FOR GRADIENT FIELD SAFETY IN AN IMPLANTABLE MEDICAL DEVICE

(75) Inventors: Lonny V. Cabelka, Chandler, AZ (US); David E. Manahan, St. Paul, MN (US); Forrest C. M. Pape, New Brighton, MN (US); John D. Wahlstrand, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/759,228

(22) Filed: Apr. 13, 2010

(65) Prior Publication Data

US 2010/0198309 A1 Aug. 5, 2010

Related U.S. Application Data

(63) Continuation of application No. 11/380,241, filed on Apr. 26, 2006, now Pat. No. 7,729,770.

(51) Int. Cl.
*A61N 1/372* (2006.01)
(52) U.S. Cl. .......................................... 607/37; 607/63
(58) Field of Classification Search ............... 607/37, 607/63, 67
See application file for complete search history.

(56) References Cited

U.S. PATENT DOCUMENTS

| | | |
|---|---|---|
| 4,320,763 A | 3/1982 | Money |
| 4,745,923 A | 5/1988 | Winstrom |
| 5,649,965 A | 7/1997 | Pons et al. |
| 5,759,197 A | 6/1998 | Sawchuk et al. |
| 6,198,972 B1 | 3/2001 | Hartlaub et al. |
| 6,414,835 B1 | 7/2002 | Wolf et al. |
| 6,580,947 B1 | 6/2003 | Thompson |
| 6,804,552 B2 | 10/2004 | Thompson et al. |
| 6,901,292 B2 | 5/2005 | Hrdlicka et al. |
| 2003/0036776 A1 | 2/2003 | Foster et al. |
| 2003/0144705 A1 | 7/2003 | Funke |
| 2004/0088012 A1 | 5/2004 | Kroll et al. |
| 2004/0267233 A1 | 12/2004 | Ginggen |
| 2005/0070975 A1 | 3/2005 | Zeijlemaker et al. |
| 2006/0064149 A1 | 3/2006 | Belacazar et al. |
| 2007/0191914 A1 | 8/2007 | Stessman |
| 2007/0255352 A1 | 11/2007 | Roline et al. |
| 2008/0039709 A1* | 2/2008 | Karmarkar ................... 600/410 |

FOREIGN PATENT DOCUMENTS

EP 0 773 449 A2 5/1997

* cited by examiner

*Primary Examiner* — Carl H Layno
*Assistant Examiner* — Luther Behringer
(74) *Attorney, Agent, or Firm* — Stephen W. Bauer; Michael J. Ostrom

(57) ABSTRACT

An implantable medical device is provided for isolating an elongated medical lead from internal device circuitry in the presence of a gradient magnetic or electrical field. The device includes an isolation circuit adapted to operatively connect an internal circuit to the medical lead in a first operative state and to electrically isolate the medical lead from the internal circuit in a second operative state.

17 Claims, 4 Drawing Sheets

ISOLATION CIRCUITRY AND METHOD FOR GRADIENT FIELD SAFETY IN AN IMPLANTABLE MEDICAL DEVICE

This application is a continuation application of U.S. patent application Ser. No. 11/380,241, filed Apr. 26, 2006 and granted as U.S. Pat. No. 7,729,770, which is incorporated by reference herein in its entirety.

TECHNICAL FIELD

The invention relates generally to implantable medical devices, and, in particular, to a method and apparatus for electrically isolating leads coupled to an implantable medical device from circuitry in the implantable medical device.

BACKGROUND

Numerous types of implantable medical devices (IMDs), such as cardiac pacemakers, implantable cardiovertor defibrillators (ICDs), neurostimulators, operate to deliver electrical stimulation therapies to excitable body tissue via associated electrodes. The electrodes are disposed at a targeted therapy delivery site and are commonly coupled to the IMD via conductors extending through elongated leads. Patients implanted with such IMDs are generally contraindicated for undergoing MRI procedures. The gradient magnetic fields that may be applied during an MRI procedure can induce current on the elongated lead conductors, which can be large enough to cause undesired stimulation of the excitable tissue in contact with the electrode(s) carried by the lead. As the number of patients having IMDs continues to grow, it is desirable to provide IMD systems that allow patients to safely undergo MRI procedures.

DETAILED DESCRIPTION

In the following description, references are made to illustrative embodiments for carrying out the invention. It is understood that other embodiments may be utilized without departing from the scope of the invention. The invention is generally directed toward providing an IMD and an associated method for protecting a patient from unwanted tissue stimulation due to current induced on implanted leads in the presence of time-varying magnetic or electrical fields, such as during MRI procedures involving gradient magnetic fields or in the presence of time-varying electrical fields associated with electronic article surveillance systems (EAS). As used herein, the term "gradient field" refers to any time varying magnetic or electrical field that is strong enough to induce current on an implanted lead and potentially cause tissue stimulation. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
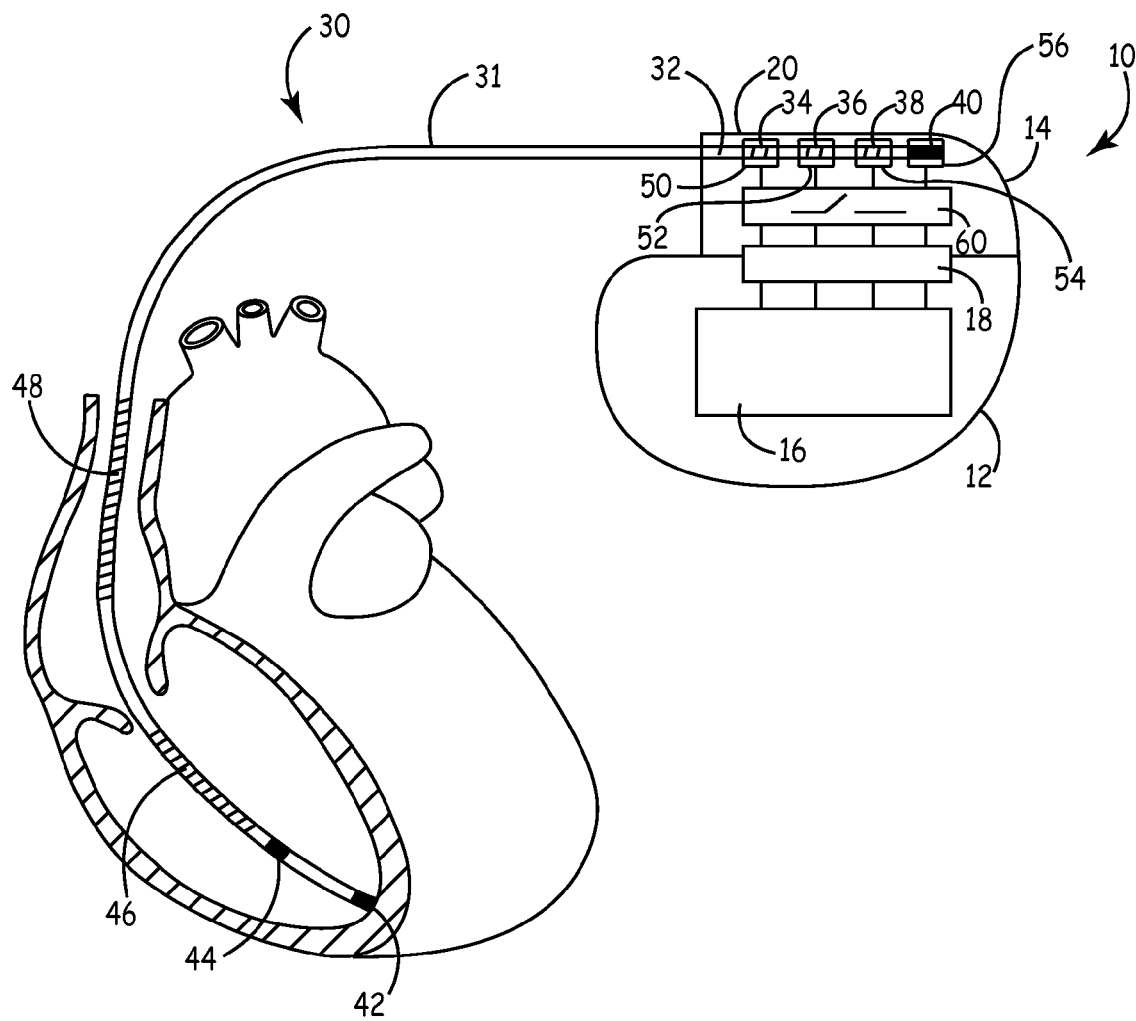
FIG. 1 is a schematic diagram of an IMD coupled to a patient's heart via a cardiac lead.

FIG. 1 is a schematic diagram of an IMD coupled to a patient's heart via a cardiac lead. IMD 10 is shown as a single chamber cardiac device, however it is recognized that various embodiments of the present invention may be implemented in single, dual, or multi-chamber cardiac devices or single or multi-channel neurostimulators. Embodiments of the present invention include IMDs provided as monitoring devices without therapy delivery capabilities. IMDs provided with therapy delivery capabilities may include, for example, cardiac pacemakers, cardioverter/defibrillators, drug delivery devices, and neurostimulators.

IMD 10 is embodied as an implantable cardioverter defibrillator (ICD) and is coupled to lead 30 for sensing cardiac signals and delivering electrical stimulation pulses to the heart in the form of cardiac pacing pulses and cardioversion/defibrillation shock pulses. Lead 30 is provided with a tip electrode 42 and ring electrode 44 which are generally used together for bipolar sensing and/or pacing functions or in combination with IMD housing 12 for unipolar sensing and/or pacing functions. Lead 30 also includes a right ventricular coil electrode 46 and a superior vena cava coil electrode 48 used in delivering high-voltage cardioversion and defibrillation shocks.

Each of the electrodes 42, 44, 46 and 48 are coupled to individual connectors 34, 36, 38 and 40 included in a proximal lead connector assembly 32 via conductors extending through elongated lead body 31. The lead connector assembly 32 is adapted for insertion into a connector bore provided in connector header 14 of IMD 10. Electrode terminals 50, 52, 54 and 56 included in connector header 14 are electrically coupled to lead connectors 34, 36, 38 and 40 when lead connector assembly 32 is fully inserted in the connector header bore.

Electrode terminals 50, 52, 54 and 56 are electrically coupled to internal IMD circuitry 16, enclosed in hermetically sealed IMD housing 12. Electrode terminals 50, 52, 54 and 56 are coupled to internal circuitry 16 via isolation circuitry 60 and protection circuitry 18, shown schematically in FIG. 1. The actual physical location of isolation circuitry 60 and protection circuitry 18 may be anywhere between electrode terminals 50, 52, 54, and 56 and any portion of the internal circuitry 16. The functionality of isolation circuitry 60 may be implemented using dedicated components or providing dual functionality of existing switching devices included in IMD 10.

Isolation circuitry 60 provides protection to the patient against unwanted tissue stimulation due to current induced on conductors carried by lead body 31. For example, in an MRI environment involving gradient magnetic fields, current induced on lead conductors can be carried along a circuit path that includes lead 30, the IMD housing 12, and body tissue. Isolation circuitry 60 interrupts this circuit path by introducing a high-impedance element as will be described in greater detail herein. Protection circuitry 18 is generally grounded to IMD housing 12 thereby providing a path from electrode terminals 50, 52, 54, and 56 to the IMD housing 12, completing the circuit pathway through the patient's body along which induced currents may be conducted. Isolation circuitry 60 is provided to open that circuit pathway to prevent unwanted tissue stimulation in an MRI or other gradient field environment.

Protection circuitry 18 is provided for eliminating or minimizing electromagnetic interference (EMI) that may be encountered in normal operating environments. EMI can produce a potential between any of electrodes 42, 44, 46 and 48 and housing 12. Circuit elements and parasitic effects provide paths for current to flow as a result of these potentials. Protection circuitry 18 prevents EMI from being coupled to the internal circuitry 16, which may otherwise cause inappropriate IMD function. Protection circuitry 18 typically includes electrically insulated, filtered feedthroughs such that electrical connections made between electrode terminals 50, 52, 54, and 56 and internal circuitry 16 are electrically isolated from IMD housing 12. The filtered feedthroughs typically include capacitive elements for filtering EMI. Examples of protection circuitry included in IMDs are generally disclosed in U.S. Pat. No. 5,759,197 (Sawchuk, et al.) and U.S. Pat. No. 6,414,835 (Wolf et al.), both of which patents are hereby incorporated in their entirety. Protection circuitry 18 may include other noise-reduction and protection networks for static discharge and other transient voltages that may arise due to EMI.

Figure 2:
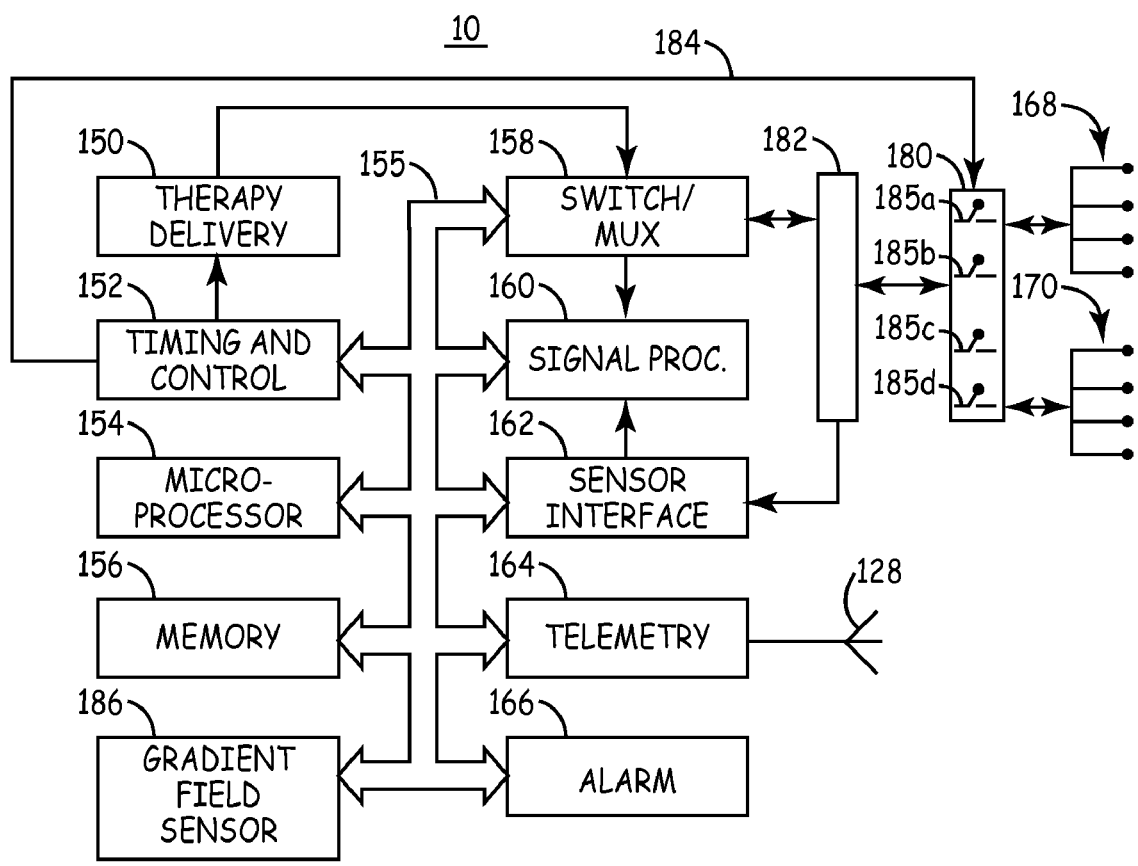
FIG. 2 is a functional block diagram of an IMD including isolation circuitry.

FIG. 2 is a functional block diagram of an IMD including isolation circuitry. IMD 10 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 10 via a data/address bus 155. IMD 10 includes therapy delivery unit 150 for delivering an electrical stimulation therapy, such as cardiac pacing therapies, under the control of timing and control 152. Therapy delivery unit 150 is typically coupled to two or more electrode terminals 168 via switch/multiplexer 158. Switch/MUX 158 is used for selecting which electrodes and corresponding polarities are used for delivering electrical stimulation pulses.

Electrode terminals 168 may also be used for receiving electrical signals from the body, such as cardiac signals or other electromyogram (EGM) signals, or for measuring impedance. In the case of cardiac stimulation devices, cardiac electrical signals are sensed for determining when an electrical stimulation therapy is needed and in controlling the timing of stimulation pulses.

Electrode terminals 168 are typically included in a connector header as described in conjunction with FIG. 1. Electrode terminals 168 may be electrically coupled to switch/MUX 158 via the isolation circuit 180 and any EMI protection circuitry 182. The remaining functional blocks shown in FIG. 2 are typically implemented on a hybrid circuit board having contact pads for making electrical connections to protection circuitry 182. Isolation circuitry 180 may be implemented anywhere between electrode terminals 168 and the connections to the various components included on a hybrid circuit board.

Isolation circuitry 180, shown as a functional block in FIG. 2, may include switching elements physically located at separate locations relative to the hybrid circuit board and IMD housing. If isolation of an associated lead from all IMD circuitry is desired, isolation circuitry 180 could be located outside the IMD housing or contained within a separate Faraday shield within the IMD housing. In other embodiments, isolation circuitry 180 may include switches used to isolate only portions of the hybrid circuitry from an associated lead and might include switching elements incorporated on the hybrid circuit board.

Switching elements already present in the IMD circuitry may be utilized to provide the isolation circuit functionality as well as other functions. For example, IMD 10 may be provided with switches used for protecting IMD circuitry from voltages produced by external defibrillation. Switches 185a through 185d may include such switches. In other words, any of switches 185a through 185d serving functionally as a part of isolation circuit 180 for protecting the patient from induced current in the presence of time-varying EM fields may be embodied as a switch already provided in IMD 10 for protecting the IMD circuitry from voltages produced by external defibrillation.

Electrodes used for sensing and electrodes used for stimulation may be selected via switch matrix 158. When used for sensing, electrode terminals 168 are coupled to signal processing circuitry 160 via switch matrix 158. Signal processor 160 includes sense amplifiers and may include other signal conditioning circuitry and an analog to digital converter. Electrical signals may then be used by microprocessor 154 for detecting physiological events, such as detecting and discriminating cardiac arrhythmias.

In some embodiments, microprocessor 154 uses signals received at electrode terminals 168 for automatically detecting induced signals associated with a gradient field, such as a time-varying magnetic field associated with MRI. Alternatively, a gradient field sensor circuit 186 may be provided for sensing external signals corresponding to a time-varying MRI or other gradient field environment. Gradient field sensor circuit 186 may be embodied according to the sensor circuit generally disclosed in U.S. Pat. No. 6,198,972 (Hartlaub et al.), hereby incorporated herein by reference in its entirety. Gradient field sensor circuit 186 may be located anywhere in a patient's body and may therefore alternatively be coupled to IMD circuitry via a sensor terminal 170. In response to a gradient field detection signal generated by gradient field sensor circuit 186, microprocessor 154 causes timing and control circuitry 152 to generate a signal on signal line 184 that opens switches 185a through 185d included in isolation circuitry 180. The circuit path through the IMD housing and the patient's body is effectively opened thereby preventing unwanted tissue stimulation due to induced currents on implanted leads coupled to IMD 10. During MRI, a sensor that detects the very strong static magnetic field may be used alone or in conjunction with other sensors to activate isolation circuitry 180

IMD 10 may additionally or alternatively be coupled to one or more physiological sensors. As such, physiological sensor terminals 170 are provided and are electrically coupled to a sensor interface 160 via protection circuitry 182. Sensor terminals 170 may also be electrically coupled to IMD circuitry, or portions of IMD circuitry, through isolation circuitry 180 when terminals 170 are coupled to elongated leads that could carry induced currents to body tissue. Physiological sensors may include pressure sensors, accelerometers, flow sensors, blood chemistry sensors, activity sensors or other physiological sensors known for use with IMDs.

Signals received at sensor terminals 170 are received by a sensor interface 162 which provides sensor signals to signal processing circuitry 160. Sensor signals are used by microprocessor 154 for detecting physiological events or conditions. For example, IMD 10 may monitor heart wall motion, blood pressure, blood chemistry, respiration, or patient activity. Monitored signals may be used for sensing the need for delivering a therapy under control of the operating system.

The operating system includes associated memory 156 for storing a variety of programmed-in operating mode and parameter values that are used by microprocessor 154. The memory 156 may also be used for storing data compiled from sensed physiological signals and/or relating to device operating history for telemetry out on receipt of a retrieval or interrogation instruction. All of these functions and operations are known in the art, and many are generally employed to store operating commands and data for controlling device operation and for later retrieval to diagnose device function or patient condition.

IMD 10 further includes telemetry circuitry 164 and antenna 128. Programming commands or data are transmitted during uplink or downlink telemetry between IMD telemetry circuitry 164 and external telemetry circuitry included in a programmer or monitoring unit. Telemetry circuitry 164 and antenna 128 may correspond to telemetry systems known in the art. In one embodiment of the invention, a gradient field mode command is transmitted to IMD telemetry circuitry 164 by a clinician or other user using an external programmer. In response to the gradient field mode command, microprocessor 154 causes timing and control circuitry 152 to generate a signal on signal line 184 to open switches included in isolation circuitry 180.

During a gradient field operating mode, electrode terminals 168 (and/or sensor terminals 170) are electrically disconnected from IMD circuitry by introducing a high-impedance element included in isolation circuitry 180. Isolation circuitry 180 generally includes switches 185a through 185d which may be embodied as electro-mechanical relays, semiconductor devices, or MEMS relays. Switches 185 included in isolation circuitry 180 may be implemented as generally described in the above-incorporated Hartlaub patent. It is recognized that each of switches 185a through 185d may include one or more electronic switches coupled in series to form a high-impedance element through isolation circuitry 180. The number of switches 185 included in isolation circuitry 180 will vary between applications and will correspond to the number of electrode terminals 168 and sensor terminals 170 that need to be electrically disconnected from the IMD ground path to prevent conduction of currents induced on elongated lead conductors during MRI procedures or in the presence of other gradient EM fields.

When microprocessor 156 determines that an electrical stimulation therapy is needed, or if an electrical stimulation therapy is in process upon initiation of the gradient field operating mode, timing and control circuitry 152 generates a transient "close" signal on signal line 184. The "close" signal is generated just prior to or contemporaneously with the generation of an electrical stimulation pulse by therapy delivery unit 150. A stimulation pulse generated by therapy delivery unit 150 is delivered to electrode terminals 168 across isolation circuitry 180. The "close" signal causes at least one switch included in isolation circuitry 180 that corresponds to a selected stimulation electrode to briefly close so that the stimulation pulse can be delivered. Other switches included in isolation circuitry 180 may remain open during stimulation pulse delivery. Accordingly, it is understood that signal line 184 may carry a multiplexed signal for operating multiple switches included in isolation circuitry 180 individually. With regard to the embodiment shown in FIG. 1, a switch coupled to electrode terminal 56 corresponding to tip electrode 42 may be controlled separately from a switch coupled to electrode terminal 54, corresponding to ring electrode 44 to allow unipolar stimulation using tip electrode 42 during a gradient field operating mode.

IMD 10 may optionally be equipped with patient alarm circuitry 166 for generating audible tones, a perceptible vibration, muscle stimulation or other sensory stimulation for notifying the patient that a patient alert condition has been detected by IMD 10. In some embodiments, an alarm signal may be generated upon detection of a gradient field or upon initiating a gradient field mode of operation.

Figure 3:
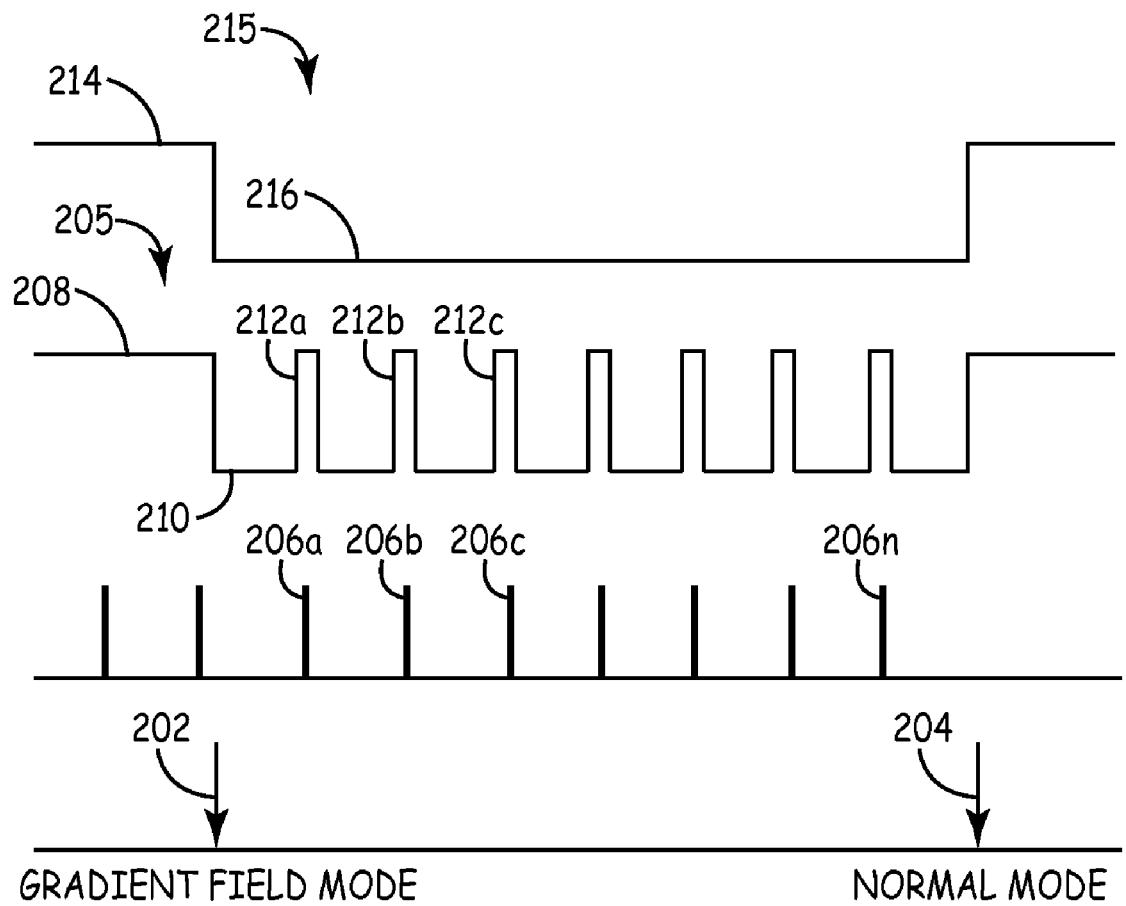
FIG. 3 is a timing diagram illustrating IMD function during a gradient field operating mode.

FIG. 3 is a timing diagram illustrating IMD function during a gradient field operating mode. At a time 202, a gradient field mode is initiated in response to a gradient field operating mode command or the automatic detection of gradient field signals, corresponding to a time-varying MRI field or other gradient EM field, by a gradient field sensor circuit. Two biasing signals 205 and 215 are provided to individual switches, for example MOSFETs, included in isolation circuitry. Initially, prior to the initiation of gradient field operating mode at time 202, the MOSFET switches are biased with high signals 208 and 214 that maintain the switches in a closed or ON operative state. For example, a MOSFET may be biased to 5.0 volts relative to circuit common to hold the transistor in the ON state to allow normal sensing and therapy delivery functions.

Upon initiation of the gradient field operating mode at time 202, biasing signals 205 and 215 are switched to low signals 210 and 216 to open the corresponding MOSFETs to an OFF operative state. For example, the MOSFETs may be biased to 0.0 volts relative to circuit common to hold the transistor in the OFF state to prevent conduction of induced currents to excitable body tissue. A feedback or bootstrap network could be used to maintain the correct state of the MOSFET.

Pacing pulses 206a, 206b, 206c through 206n are delivered after the initiation of gradient field mode at time 202. Pacing therapy may have been in progress at the time of initiating the gradient field mode or a need for pacing therapy may be detected during the gradient field mode using other sensors or circuits that are not opened by isolation circuitry. In pacing dependent patients, initiation of the gradient field mode may include maintaining a predetermined pacing rate. Reference is made to U.S. Pat. App. Pub. No. 2003/0144705 (Funke), hereby incorporated herein by reference in its entirety. Intrinsic cardiac signals may be sensed during the gradient field operating mode through high impedance signal path sensing channels or utilize a gradient energy cancellation sensing method.

In order to deliver pacing pulses 206a through 206n, at least one switch (for unipolar pacing) included in isolation circuitry is transiently closed by generating a high biasing signal 212a, 212b, 212c, 212n at appropriate times relative to pacing pulses 206a through 206n. In order to deliver bipolar pacing pulses, two switches may be transiently closed during pacing pulse delivery. Timing and control module 152 (FIG. 2) controls the alternation between high and low bias signal levels applied to isolation circuit switches to control the operative state of the switches. A switch is closed to close a pacing or electrical stimulation circuit at appropriate times during the gradient field mode to allow therapeutic stimulation to be performed, for example during MRI procedures. The switch(es) included in a pacing or electrical stimulation circuit are briefly closed for an interval of time starting just prior to or approximately the same time as a stimulation pulse and extending for a time at least equal to the stimulation pulse width. While the timing diagram shown in FIG. 3 illustrates the delivery of cardiac pacing pulses, it is recognized that any type of electrical stimulation pulses may be delivered during a gradient field mode by controlling the opening and closing of switches included in isolation circuitry. For example the need for high-voltage cardioversion/defibrillation shocks may be detected based on sensing intrinsic signals using a gradient energy cancellation method and high energy therapies may be delivered based on determining a reliable sensing signal for arrhythmia detection.

Figure 4:
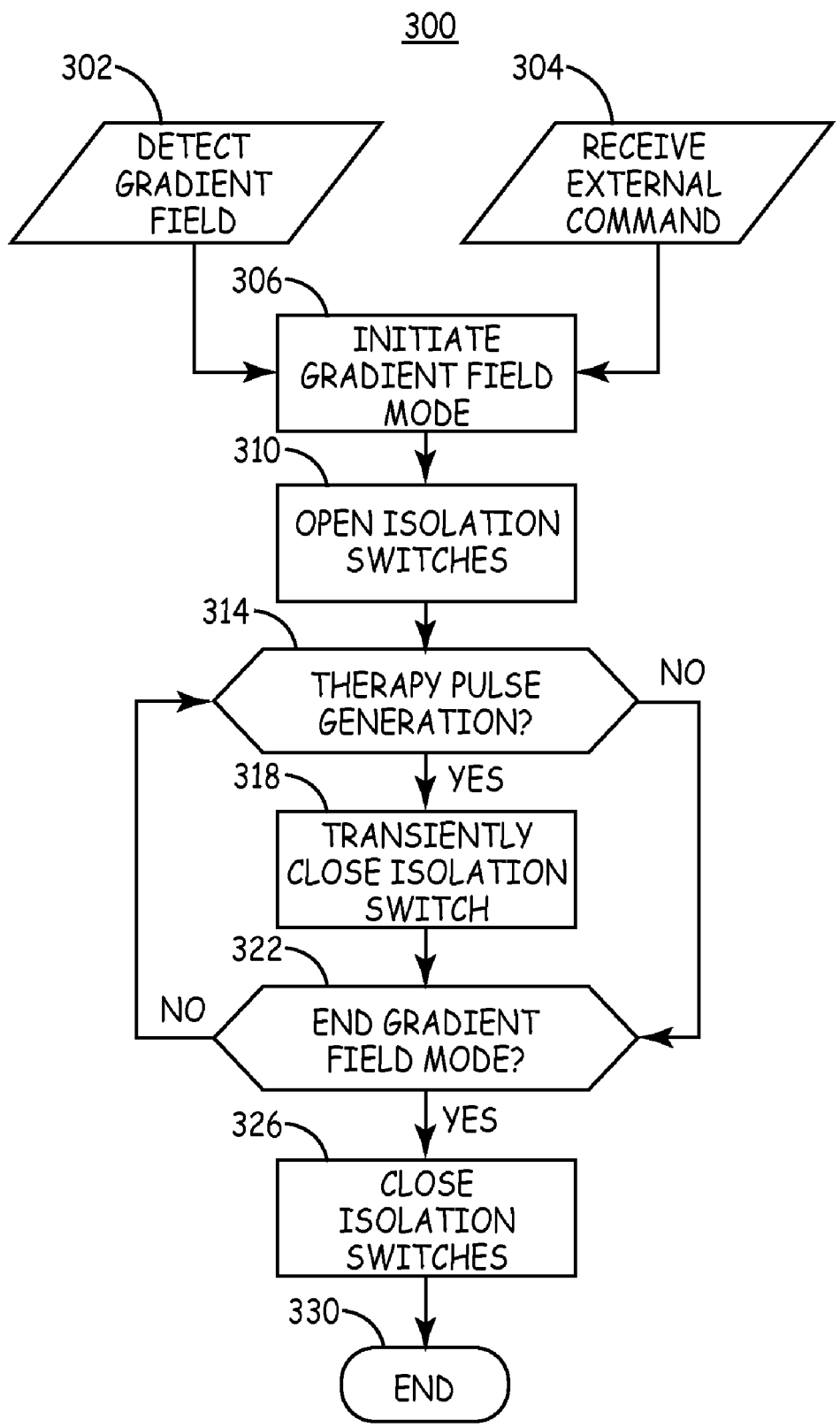
FIG. 4 is a flow chart summarizing one method for controlling isolation circuitry included in an IMD.

FIG. 4 is a flow chart summarizing one method for controlling isolation circuitry included in an IMD. Flow chart 300 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software and/or hardware to accomplish the present invention in the context of any modern IMD, given the disclosure herein, is within the abilities of one of skill in the art.

The IMD microprocessor initiates a gradient field operating mode at block 306. The gradient field operating mode is initiated in response to receipt of an external command provided to the IMD using a programmer or other device enabled for telemetric communication with the IMD (block 304). The gradient field operating mode is alternatively initiated in response to the detection of external or internal high level signals corresponding to an MRI or other time-varying EM environment by gradient field sensor circuit at block 302.

Upon initiation of the gradient field mode, switches included in isolation circuitry are opened at block 310. A gradient magnetic field may induce currents on implanted lead conductors large enough to cause tissue stimulation. Opening of isolation circuitry switches opens the circuit path through the capacitive feedthrough elements and the IMD housing and patient's body, preventing conduction of induced currents and unwanted tissue stimulation.

At decision block 314, timing and control module 152 determines if a therapeutic stimulation pulse is needed based on programmed therapy delivery mode. Upon triggering the generation of a therapy stimulation pulse, timing and control 152 generates a signal to transiently close one or more isolation circuitry switches included in a stimulation circuit path in order to allow stimulation pulse delivery at block 318.

Throughout the gradient field mode, the IMD microprocessor monitors for receipt of an external command indicating that a normal operating mode should be restored at decision block 322. Additionally or alternatively, the IMD microprocessor automatically monitors for an end to the detection of gradient signals by a gradient field sensor. In other embodiments, the gradient field mode may be maintained for a fixed interval of time after gradient field mode initiation. For example, the gradient field mode may be maintained for 30 minutes, one hour, or another interval of time that is expected to extend safely beyond the completion of an MRI procedure. As long as the gradient field mode is maintained, timing and control module 152 continues to control transient closure of stimulation circuit path switches included in isolation circuitry contemporaneously with the generation of therapeutic stimulation pulses at block 318.

Upon expiration of the gradient field mode according to a predetermined time interval, receipt of an external termination command, or loss of gradient field signal detection at decision block 318, isolation circuitry switches are closed at block 326. Closure of isolation switches restores normally closed sensing and stimulation circuit paths for normal IMD operation. The gradient field operation mode is then terminated at block 330.

Thus, an IMD and associated methods for protecting a patient from unwanted tissue stimulation during exposure to time-varying electrical or magnetic fields has been presented in the foregoing description with reference to specific embodiments. It is appreciated that various modifications to the referenced embodiments may be made without departing from the scope of the invention as set forth in the following claims.

The invention claimed is:

1. A method of operating an implantable medical device comprising:
electrically disconnecting an internal circuit from electrical conductors of at least one elongated medical lead in response to a command received from an external device or in response to detection of signals corresponding to a time varying electromagnetic environment to initiate a gradient field operating mode;
determining that an electrical stimulation therapy is needed while operating in the gradient field operating mode; and
transiently connecting the internal circuit to at least a portion of the electrical conductors of the at least one elongated medical lead to deliver the electrical stimulation therapy while operating in the gradient field operating mode.

2. The method of claim 1, wherein transiently connecting the internal circuit to at least a portion of the electrical conductors comprises transiently connecting the internal circuit to at least a portion of the electrical conductors for an interval of time starting just prior to or approximately the same time as the electrical stimulation pulse and extending for a time at least equal to the stimulation pulse width.

3. The method of claim 1, further comprising:
sensing signals corresponding to a gradient field environment,
wherein electrically disconnecting the internal circuit from the electrical conductors of the at least one elongated medical lead comprises electrically disconnecting the internal circuit from electrical conductors of the at least one elongated medical lead to initiate the gradient field operating mode in response to sensing the external signals corresponding to a gradient field environment.

4. The method of claim 1, further comprising:
sensing one or more physiological signals of a patient while operating in the gradient field operating mode,
wherein determining that the electrical stimulation therapy is needed while operating in the gradient field operating mode comprises determining that the electrical stimulation therapy is needed based on the one or more sensed physiological signals.

5. The method of claim 4, wherein sensing one or more physiological signals comprises sensing one of heart wall motion, blood pressure, blood chemistry, respiration, or patient activity.

6. The method of claim 1, wherein determining that the electrical stimulation therapy is needed comprises determining that the electrical stimulation therapy is needed while operating in the gradient field operating mode when the electrical stimulation therapy is in process upon initiation of the gradient field operating mode.

7. The method of claim 1, wherein transiently connecting the internal circuit to at least a portion of the electrical conductors of the at least one elongated medical lead comprises transiently connecting the internal circuit to one or more electrical conductors corresponding to one or more electrodes via which the electrical stimulation therapy is delivered.

8. The method of claim 7, further comprising continuing to electrically disconnect the other electrical conductors during delivery of the electrical stimulation therapy.

9. The method of claim 1, further comprising electrically connecting the internal circuit to the electrical conductors upon expiration of the gradient field operating mode.

10. An implantable medical device comprising:
an internal circuit adapted to generate an electrical stimulation therapy;
an isolation circuit adapted to connect the internal circuit to one or more electrical conductors of at least one medical lead; and a control module configured to control the isolation circuit to electrically disconnect the internal circuit from the one or more electrical conductors of the at least one lead in response to a command received from an external device or in response to detection of signals corresponding to a time varying electromagnetic environment to initiate a gradient field operating mode; determine that an electrical stimulation therapy is needed while operating in the gradient field operating mode, and transiently connect the internal circuit to at least a portion of the one or more electrical conductors of the at least one lead to deliver the electrical stimulation therapy while operating in the gradient field operating mode.

11. The device of claim 10, wherein the control module controls the isolation circuit to transiently connect the internal circuit to at least a portion of the one or more electrical conductors for an interval of time starting just prior to or approximately the same time as delivery of the electrical stimulation pulse and extending for a time at least equal to a stimulation pulse width.

12. The device of claim 10, further comprising:
a sensor circuit to sense signals corresponding to a gradient field environment,
wherein the control unit electrically disconnects the internal circuit from the electrical conductors of the at least one elongated medical lead to initiate the gradient field operating mode in response to the signals sensed by the sensor circuit.

13. The device of claim 10, further comprising:
a physiological sensor to sense one or more physiological signals of a patient while operating in the gradient field operating mode,
wherein the control unit determines that the electrical stimulation therapy is needed while operating in the gradient field operating mode based on the one or more sensed physiological signals.

14. The device of claim 13, wherein the physiological sensor comprises at least one of a pressure sensor, accelerometer, flow sensor, blood chemistry sensor, or activity sensor.

15. The device of claim 10, wherein the control unit transiently connects the internal circuit to one or more electrical conductors corresponding to one or more electrodes via which the electrical stimulation therapy is delivered while continuing to electrically disconnect the other electrical conductors during delivery of the electrical stimulation therapy.

16. The device of claim 10, further comprising electrically connecting the internal circuit to the electrical conductors upon expiration of the gradient field operating mode.

17. An implantable medical device comprising:
means for electrically disconnecting an internal circuit from electrical conductors of at least one elongated medical lead in response to a command received from an external device or in response to detection of signals corresponding to a time varying electromagnetic environment to initiate a gradient field operating mode;
means for determining that an electrical stimulation therapy is needed while operating in the gradient field operating mode; and
means for transiently connecting the internal circuit to at least a portion of the electrical conductors of the at least one elongated medical lead to deliver the electrical stimulation therapy while operating in the gradient field operating mode.

* * * * *